US012642894B2

(12) United States Patent
Ochiai et al.

(10) Patent No.: US 12,642,894 B2
(45) Date of Patent: Jun. 2, 2026

(54) BREAST PUMP

(71) Applicant: Pigeon Corporation, Tokyo (JP)

(72) Inventors: Yukifumi Ochiai, Tokyo (JP);
Yoshihiro Shimomura, Chiba (JP);
Yuina Ando, Chiba (JP); Hyunjin Im,
Chiba (JP); Hayato Ueno, Chiba (JP);
Tsukasa Hattori, Chiba (JP)

(73) Assignee: Pigeon Corporation, Tokyo (JP)

( * ) Notice: Subject to any disclaimer, the term of this
patent is extended or adjusted under 35
U.S.C. 154(b) by 1040 days.

(21) Appl. No.: 17/760,755

(22) PCT Filed: Sep. 20, 2019

(86) PCT No.: PCT/JP2019/037034
§ 371 (c)(1),
(2) Date: Mar. 15, 2022

(87) PCT Pub. No.: WO2021/053819
PCT Pub. Date: Mar. 25, 2021

(65) Prior Publication Data
US 2022/0339330 A1 Oct. 27, 2022

(51) Int. Cl.
*A61M 1/06* (2006.01)

(52) U.S. Cl.
CPC .............. *A61M 1/06* (2013.01); *A61M 1/062*
(2014.02); *A61M 2205/586* (2013.01)

(58) Field of Classification Search
CPC .......................................... A61M 1/06–10697
See application file for complete search history.

(56) References Cited

U.S. PATENT DOCUMENTS 8,187,219 B1 * 5/2012 Chiang ................. A61M 1/064
604/74
2020/0171223 A1 6/2020 Ochiai et al.

FOREIGN PATENT DOCUMENTS

JP 2019010350 A 1/2019

OTHER PUBLICATIONS

International Application No. PCT/JP2019/037034, Search Report
mailed May 11, 2019 (English translation), 1 pg.

* cited by examiner

*Primary Examiner* — Courtney B Fredrickson
(74) *Attorney, Agent, or Firm* — Schwegman Lundberg &
Woessner, P.A.

(57) ABSTRACT

A breast pump includes a main body and a handle. The main
body includes an internal passage, a negative pressure
generation mechanism configured to generate negative pres-
sure in the internal passage for pumping milk, a hood
attaching portion to which a hood fitted to a breast is
attached, the hood attaching portion being disposed at a front
part of the main body, and a bottle attaching portion to which
a bottle for collecting milk is attached, the bottle attaching
portion being disposed at a lower part of the main body. The
handle is pivotal to the main body and includes a basal end,
at a side located closer to a pivot point on the main body,
connected to the negative pressure generation mechanism.
The handle includes a finger rest at a distal side and extends
forward from the pivot point beside the main body.

6 Claims, 7 Drawing Sheets

Fig.6A
Fig.6B
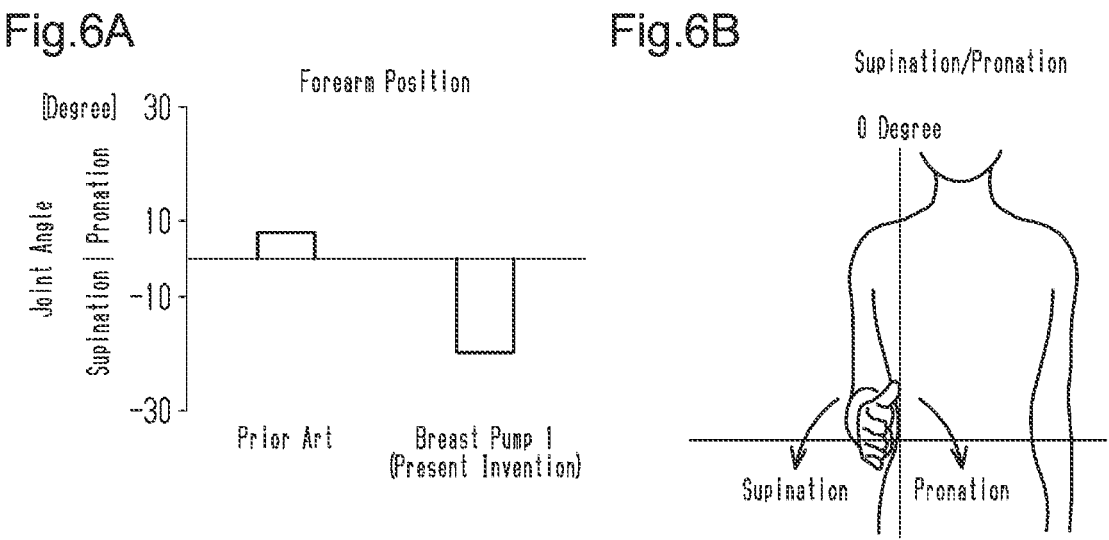
Fig.7
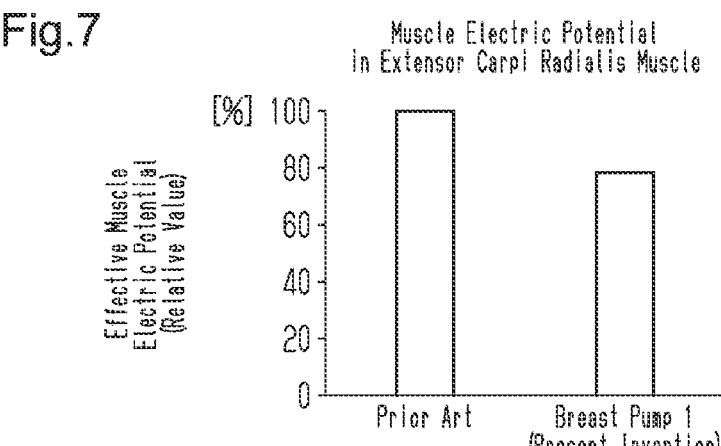
Fig.8
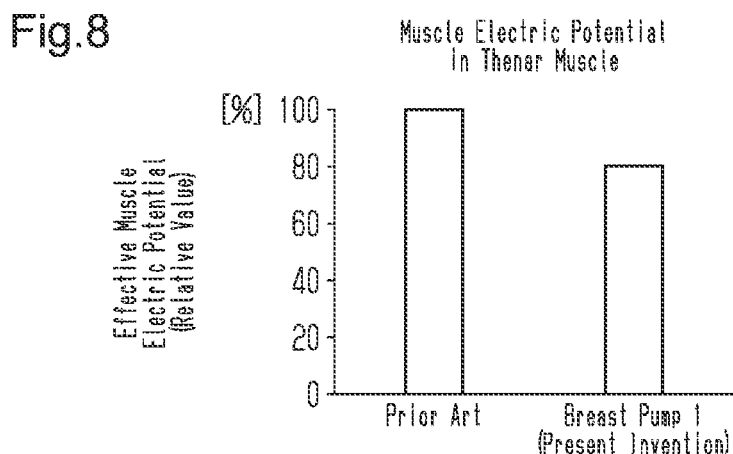

BREAST PUMP

This application is a U.S. National Stage Filing under 35 U.S.C. 371 from International Application No. PCT/JP2019/037034, filed on Sep. 20, 2019, and published as WO 2021/053819 A1 on Mar. 25, 2021, which is incorporated by reference herein in its entirety.

TECHNICAL FIELD

The present disclosure relates to a breast pump for manually pumping milk.

BACKGROUND ART

Patent Literature 1 describes an example of a breast pump that includes a main body and a manually-operated handle. A hood and a bottle are attached to the main body. The hood is fitted to a breast, and the bottle collects milk. The handle is attached to the main body in a pivotal manner. The main body includes an internal passage and a diaphragm. The internal passage connects a milking port and the bottle. The diaphragm causes the pressure of the internal passage to become negative. The handle is supported by an upper part of the main body in a pivotal manner and extends downward toward the bottle. The hood is fitted to a breast and four fingers other than the thumb are placed on the handle with the thumb placed on the main body to pivot the handle toward the main body. This lifts and deforms the diaphragm so that the pressure of the internal passage becomes negative. Thus, the milk extracted from the nipple flows into the internal passage.

CITATION LIST

Patent Literature

Patent Literature 1: Japanese Patent Application Laid-Open No. 2019-10350

SUMMARY OF INVENTION

Technical Problem

Milk-pumping may continue for as much as ten minutes. Accordingly, it is desired that the load applied to the muscles of the forearm and hand be reduced.

An objective of the present disclosure is to provide a breast pump that reduces the load applied to the muscles of the forearm and hand during milk-pumping.

Solution to Problem

A breast pump that solves the above problem includes a main body and a handle. The main body includes an internal passage and a negative pressure generation mechanism. The negative pressure generation mechanism is configured to generate negative pressure in the internal passage for pumping milk. The main body includes a hood attaching portion to which a hood fitted to a breast is attached. The hood attaching portion is disposed at a front part of the main body. The main body includes a bottle attaching portion to which a bottle for collecting milk is attached. The bottle attaching portion is disposed at a lower part of the main body. The handle is pivotal to the main body and includes a basal end, at a side located closer to a pivot point on the main body, connected to the negative pressure generation mechanism.

The handle includes a finger rest at a distal side and extends forward from the pivot point beside the main body. This structure allows the user to pump milk in a supination position and reduces the load applied to the muscles of the forearm such as the extensor carpi radialis muscle. Further, the forearm is in contact with the body trunk below the breast so that the forearm position is readily maintained.

In the breast pump, the handle may include a finger bump arranged at a side of the finger rest adjacent to the pivot point. This structure allows the user to operate the handle with four fingers excluding the thumb. The finger bump avoids the side (base) of the index finger from contacting the main body.

In the breast pump, the finger rest may be entirely linear or include at least a part curved toward the hood. This structure, particularly when the finger rest includes a part curved toward the hood, allows the little finger to be located close to the thenar eminence for handle operation.

In the breast pump, the main body may include a support disposed below the hood. This structure allows the user to place the thenar muscle region on the support so that the load applied to the thenar muscle is reduced.

In the breast pump, the support may be a restriction configured to limit a pivoting range of the handle. This structure stops excess pivoting of the handle.

In the breast pump, the main body may include a recess formed between the bottle attaching portion and the support. With this structure, the base of the index finger will not meet the main body. Further, the position of the breast pump will be stable during milk-pumping.

In the breast pump, the negative pressure generation mechanism may include a diaphragm and an insertion portion. The diaphragm closes an end of the internal passage and is connected to the handle. The diaphragm is configured to generate negative pressure in the internal passage. The insertion portion is inserted into the internal passage and connected to the diaphragm. This structure limits movement of the insertion portion in the internal passage and thus the position of the pivoted handle will be stable.

Advantageous Effects of Invention

The present invention reduces the load applied to the muscles of the forearm and hand during milk-pumping.

BRIEF DESCRIPTION OF DRAWINGS

FIG. 6A is a diagram showing a forearm position when using a conventional breast pump in a pronation position and when using a breast pump according to the present invention in a supination position.

FIG. 6B is a diagram illustrating the supination position and the pronation position.

FIG. 7 is a diagram showing a muscle electric potential in the extensor carpi radialis muscle when using the conventional breast pump in the pronation position and when using the breast pump according to the present invention in the supination position.

FIG. 8 is a diagram showing the muscle electric potential in the thenar muscle when using the conventional breast pump in the pronation position and when using the breast pump according to the present invention in the supination position.

DESCRIPTION OF EMBODIMENT

A breast pump will now be described with reference to FIGS. 1 to 5.

Figure 1:
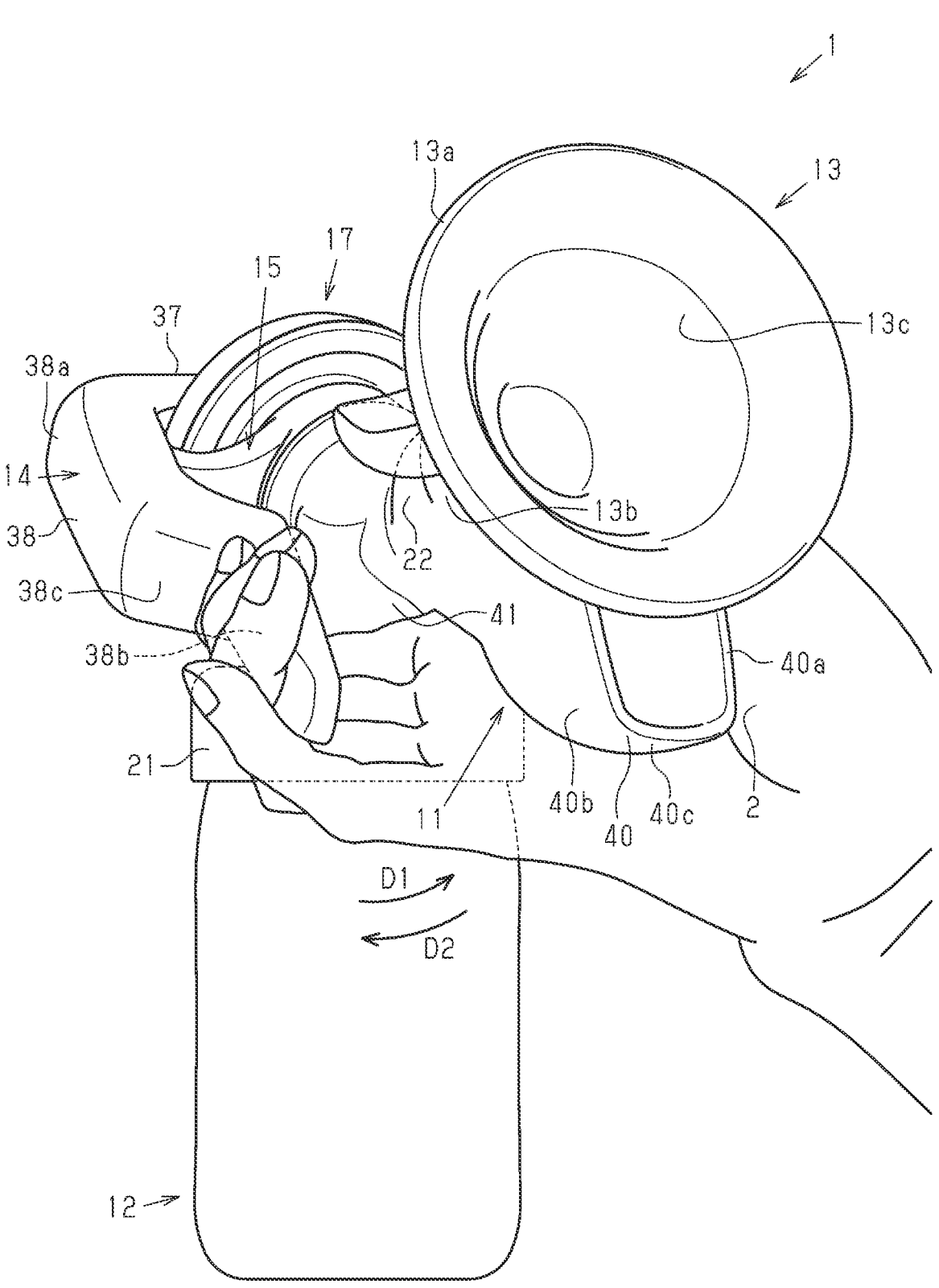
FIG. 1 is a perspective view showing a breast pump in use.

As shown in FIG. 1, a breast pump 1 is a manual breast pump that is sized so that a user can operate it with one hand in a supination position in which the palm of the user is faced upward. The breast pump 1 includes a main body 11, a bottle 12, a hood 13, a handle 14, and a handle base 15. Hereinafter, the direction of the hood 13 from the main body 11 will be defined as the forward direction, and the direction of the pivot point of the handle 14 as viewed from the main body 11 will be defined as the rearward direction. Further, the direction of the attached bottle 12 from the main body 11 will be defined as the downward direction, and the direction extending opposite the bottle 12 will be defined as the upward direction. Furthermore, the direction of the handle 14 from the main body 11 and the opposite direction will be defined as the sideward directions.

The main body 11 is a member to which the bottle 12 is connected and the hood 13 is attached. The bottle 12 collects milk. The main body 11 is a molded product of a synthetic resin material that is hard and light in weight. Specifically, the main body 11 is formed from a synthetic resin material such as polypropylene, polycarbonate, polycycloolefin, polyethersulfone, and/or polyphenylsulfone.

Figure 2:
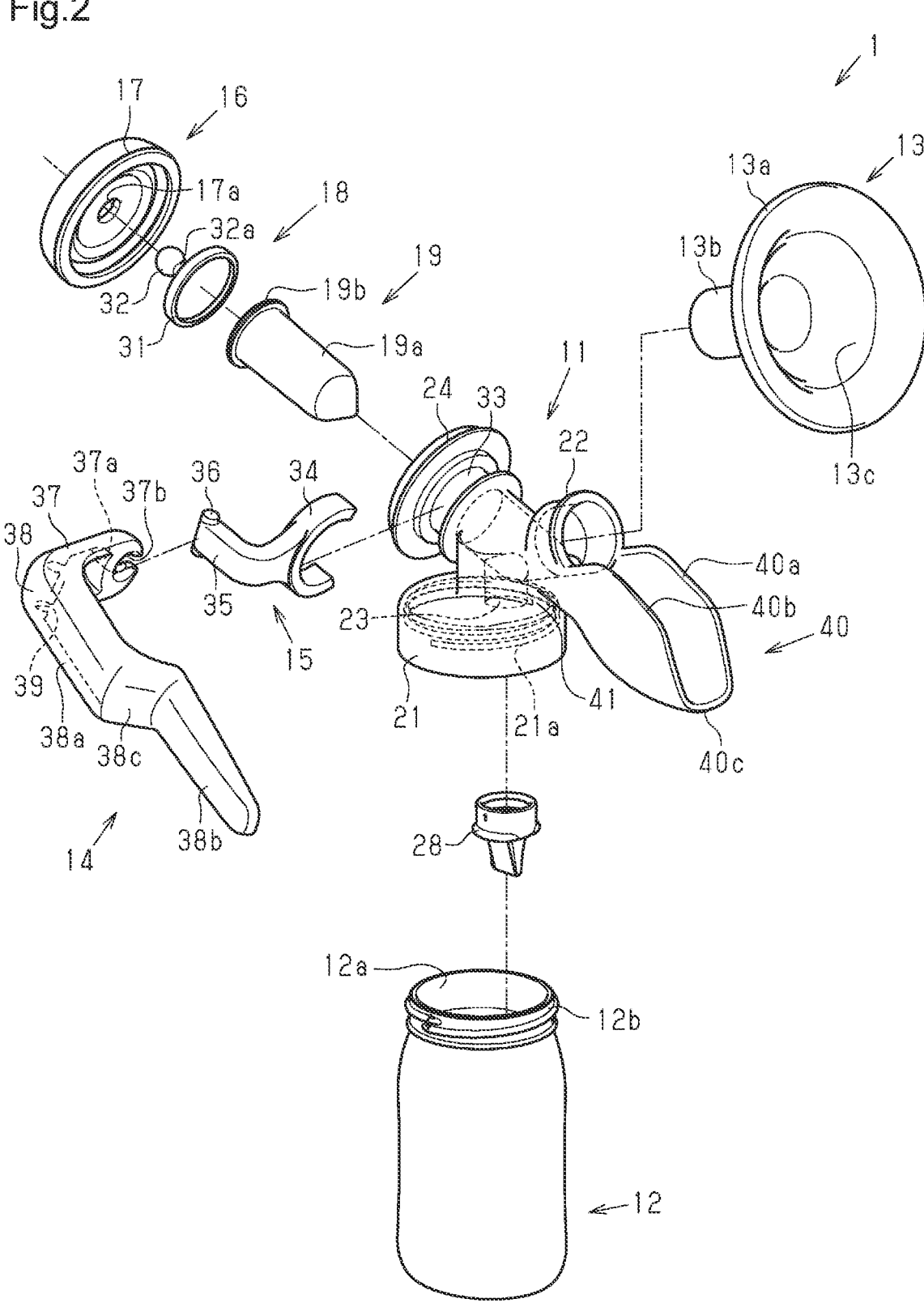
FIG. 2 is an exploded perspective view of the breast pump shown in FIG. 1.

As shown in FIG. 2, the main body 11 includes a bottle attaching portion 21, a hood attaching portion 22, and an internal passage 23. The bottle attaching portion 21 is located at a lower part of the main body 11. The bottle 12 is a container that collects milk and includes an open bottle portion 12a. An external thread 12b is formed in the outer circumferential surface of the circumferential wall of the open bottle portion 12a. When an artificial nipple is attached to the open bottle portion 12a instead of the main body 11, the bottle 12 can be used as a feeding bottle. The bottle attaching portion 21 includes a recess allowing the open bottle portion 12a to be fastened therein. The inner circumferential surface of the bottle attaching portion 21 includes an internal thread 21a that can be mated with the external thread 12b.

The hood attaching portion 22 is cylindrical and located diagonally upward of the bottle attaching portion 21. The hood 13 is dome-shaped or horn-shaped in correspondence with the shape of a breast. The hood 13 includes a large-diameter portion 13a and a cylindrical portion 13b. The large-diameter portion 13a is fitted to a breast. The cylindrical portion 13b is arranged at the peak of the large-diameter portion 13a. The large-diameter portion 13a includes a milking port 13c. In the large-diameter portion 13a, an elastic pad or the like is attached to the edge of the open end so that the large-diameter portion 13a can be tightly fitted to the breast. The cylindrical portion 13b is inserted into and fitted in the hood attaching portion 22.

Figure 3:
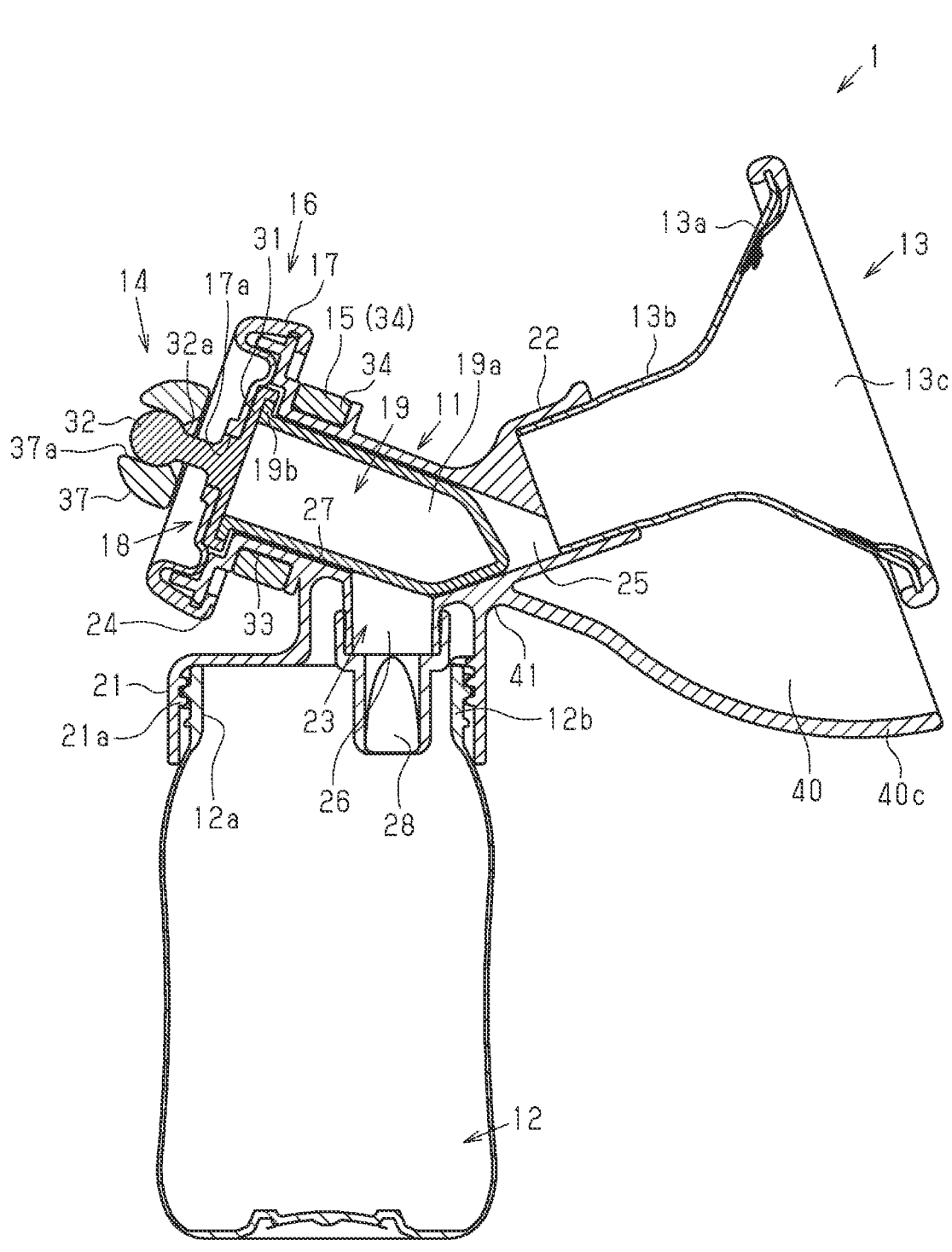
FIG. 3 is a cross-sectional view of the breast pump shown in FIG. 1 when an internal passage is in a normal pressure state.

As shown in FIG. 3, the internal passage 23 is arranged inside the main body 11. The internal passage 23 extends between and connects the bottle attaching portion 21 and the hood attaching portion 22. Further, the internal passage 23 extends toward an attachment end 24 where a diaphragm 17 is attached. In other words, the internal passage 23 extends between and connects the bottle attaching portion 21, the hood attaching portion 22, and the attachment end 24. The internal passage 23 includes an inflow passage 25, a temporary reservoir 26, and a negative pressure generation passage 27.

The inflow passage 25 connects the hood attaching portion 22 and the temporary reservoir 26 and extends downward to the temporary reservoir 26. The temporary reservoir 26 is located at the inner side of the bottle attaching portion 21 and extends downward. The temporary reservoir 26 is an open area for temporarily collecting the milk flowing from the inflow passage 25 when negative pressure is generated.

A valve member 28 is attached to the lower end of the temporary reservoir 26 inside the open bottle portion 12a. The valve member 28 is a check valve, for example, a duckbill valve. The valve member 28 checks backflow of milk and air from the bottle 12 to the main body 11. Also, the valve member 28 partitions the internal passage 23 and the interior of the bottle 12 to form a negative pressure state in the internal passage 23. The valve member 28 is formed from a synthetic resin material that is flexible and elastic, such as silicone rubber and/or elastomer, or natural rubber.

The valve member 28 includes a pair of flexible flaps, and a slit is formed between the flaps. When the internal passage 23 is in a negative pressure state, the flaps of the valve member 28 abut each other and close the slit. This closes the lower end of the temporary reservoir 26 to temporarily collect the milk flowing from the inflow passage 25. When the pressure of the internal passage 23 becomes normal, the flaps separate from each other and open the slit. This connects the temporary reservoir 26 and the inside of the bottle 12 so that the milk collected in the temporary reservoir 26 flows into the bottle 12.

The negative pressure generation passage 27 is separate from the inflow passage 25 and branched off from the temporary reservoir 26. Specifically, the negative pressure generation passage 27 extends diagonally upward from the upper end of the temporary reservoir 26 or the portion connecting the inflow passage 25 and the temporary reservoir 26 in the direction opposite to the inflow passage 25. The negative pressure generation passage 27 is larger than the inflow passage 25 in diameter. Further, the negative pressure generation passage 27 is larger than the temporary reservoir 26 in diameter. The negative pressure generation passage 27 has a diameter allowing a user to insert, for example, a finger. The upper end of the negative pressure generation passage 27 corresponds to the attachment end 24 where the diaphragm 17 is attached. The attachment end 24 is flanged and extends outward to increase the area of the opening.

The internal passage 23 includes a negative pressure generation mechanism 16 to cause the pressure of the internal passage 23 to become negative. The negative pressure generation mechanism 16 includes the diaphragm 17, a lift plate 18, and an insertion member 19.

The diaphragm 17 is a negative pressure generation member that causes the pressure of the internal passage 23 to become negative. The diaphragm 17 is formed from a synthetic resin material that is flexible and elastic such as silicone rubber, and/or elastomer, or natural rubber. The diaphragm 17 is arranged to close the attachment end 24. The internal passage 23 includes three ends, namely, the end of the inflow passage 25 where the hood 13 is attached, the lower end of the temporary reservoir 26 where the valve member 28 is attached, and the attachment end 24 where the diaphragm 17 is attached. When the hood 13 is fitted to a breast and the milking port 13c is closed, that is, the end of the inflow passage 25 is closed, the other ends, which are the lower end of the temporary reservoir 26 and the attachment end 24, are respectively closed by the valve member 28 and the diaphragm 17. Thus, the internal passage 23 becomes a substantially sealed space. The lift plate 18 is arranged on the diaphragm 17 and serves as a connecting portion that connects to the handle 14.

The lift plate 18 is a molded body of a synthetic resin material that is harder than the diaphragm 17. The lift plate 18 is formed from a synthetic resin material such as polycarbonate, polycycloolefin, polyethersulfone, and/or polyphenylsulfone. The lift plate 18 is a portion connecting to the handle 14 and includes a plate portion 31 and a connection projection 32. The plate portion 31 is arranged on the inner surface of the diaphragm 17. The connection projection 32 projects from a central part of the surface of the plate portion 31 that faces the diaphragm 17. The central part of the diaphragm 17 includes a through hole 17a through which the connection projection 32 projects outward from the diaphragm 17. The connection projection 32 has a spherical tip and an engagement groove 32a that is formed in the lower end of the sphere.

The insertion member 19 is attached to the plate portion 31. The insertion member 19 includes an insertion portion 19a and an attachment flange 19b. The attachment flange 19b is attached to and overlapped with the plate portion 31. In an example, the attachment flange 19b may be fixed to the plate portion 31 with an adhesive or the like. Alternatively, the outer circumferential portion of the attachment flange 19b may be engaged with an engagement piece arranged on the plate portion 31. Furthermore, the attachment flange 19b may be integrated into the plate portion 31 through a welding process such as ultrasonic welding or heat-welding.

The insertion portion 19a is a cylindrical portion projecting from the attachment flange 19b. The insertion portion 19a is inserted into the negative pressure generation passage 27 and acts as a volume reduction portion that reduces the volume of the negative pressure generation passage 27. The insertion portion 19a has a diameter such that a slight gap is formed between the outer circumferential surface of the insertion portion 19a and the inner circumferential surface of the negative pressure generation passage 27. The insertion portion 19a projects from the attachment flange 19b and is inserted into the interior space of the negative pressure generation passage 27. The projecting shape of the insertion portion 19a corresponds to the internal shape of the negative pressure generation passage 27, into which the insertion portion 19a is inserted. In an example, the insertion portion 19a is a projection portion that has the form of a column or a cylinder with a closed end. In an example, the negative pressure generation passage 27 has the form of a hollow cylinder and includes an interior space. The insertion portion 19a is set to have an outer diameter that is smaller than the inner diameter of the negative pressure generation passage 27.

When the negative pressure generation passage 27 is inserted, the gap allows the insertion portion 19a to smoothly move upward and downward even if the insertion portion 19a is slightly tilted with respect to the negative pressure generation passage 27. Further, the insertion portion 19a has a length set such that the insertion portion 19a will not close the outlet of the inflow passage 25 leading to the temporary reservoir 26 when the diaphragm 17 is lifted.

Thus, when negative pressure is generated, milk flows from the inflow passage 25 into the temporary reservoir 26. The insertion portion 19a has a length set such that the insertion portion 19a will be located at the outlet of the inflow passage 25 or the upper end of the temporary reservoir 26 when the diaphragm 17 is not deformed. Also, the distal end of the insertion portion 19a has a protruding triangular shape that substantially closes the outlet of the inflow passage 25.

The handle 14 is supported by the handle base 15 and pivots relative to the main body 11. The handle base 15 is attached in a rotatable manner to a cylindrical bottom part of the attachment end 24 of the diaphragm 17. The handle base 15 includes an attachment portion 34 and a pivot support piece 35. The attachment portion 34 is C-shaped. The bottom part of the attachment end 24 includes a groove-like guide portion 33 extending in a circumferential direction. The attachment portion 34 is fitted to the guide portion 33 in a manner rotatable in the circumferential direction. Thus, the position of the handle 14 is adjusted relative to the main body 11 in conformance with the body, hand size, forearm length, and the like of a user. The pivot support piece 35 is a C-shaped elongated piece that extends from the attachment portion 34 to a position upward of the diaphragm 17. The distal end of the pivot support piece 35 includes a pivot shaft 36 that pivotally supports the handle 14.

The handle 14 is formed from a synthetic resin material such as polycarbonate, polycycloolefin, polyethersulfone, and/or polyphenylsulfone. The handle 14 includes a lifter 37 and a lever 38. The lifter 37 pulls the diaphragm 17 using the lift plate 18 and includes a pit 37a. The bottom surface of the pit 37a includes an engagement hole 37b. The connection projection 32 of the lift plate 18 is inserted through the engagement hole 37b so that the edge of the engagement hole 37b engages the engagement groove 32a. In this manner, the handle 14 is connected to the diaphragm 17 by the lift plate 18 so that the diaphragm 17 can be lifted. Further, the handle 14 is rotatable relative to the connection projection 32.

The lever 38 is used as a grip and extends forward in the same manner as the hood 13. The hood 13 extends diagonally upward from the main body 11, whereas the lever 38 extends diagonally downward beside the main body 11. The handle 14 has a curved outer surface to allow for easy handling and is held by the user with fingers other than the thumb. The lever 38 includes a curved part 38a and a finger rest 38b. The curved part 38a is bulged outward from the lifter 37. The finger rest 38b is continuous with the curved part 38a. A finger bump 38c is arranged between the curved part 38a and the finger rest 38b. The finger rest 38b is linear and has a length allowing for at least four fingers excluding the thumb to rest thereon. The finger bump 38c is a raised portion located adjacent to the pivot point side of the finger rest 38b and comes into contact with the side of the index finger. Thus, the finger rest 38b allows the handle to be operated with four fingers excluding the thumb.

The inner side of the curved part 38a avoids the diaphragm 17 and the attachment end 24. A shaft support 39 is arranged at the inner side of the handle 14 near the boundary between the lever 38 and the lifter 37 and engaged with the pivot shaft 36. When the pivot shaft 36 is pivotally engaged with the shaft support 39, the handle 14 is supported and pivots relative to the main body 11. This portion serves as the pivot point of the handle 14. The handle 14 is moved back and forth about the pivot point. The handle 14 is manually pivoted in arrowed direction D1 that is a pivot operation direction, and the handle 14 is pivoted by the resiliency of the diaphragm 17 in arrowed direction D2 that is a recovery direction.

In the main body 11, a support 40 is arranged below the hood 13. The support 40 is formed integrally with the hood attaching portion 22 and protrudes from the hood attaching portion 22. The support 40 includes two vertical walls 40a and 40b and a horizontal wall 40c. The two vertical walls 40a and 40b extend downward from the hood attaching portion 22. The horizontal wall 40c connects the lower ends of the two vertical walls 40a and 40b. The two vertical walls 40a and 40b are, for example, flat plates. The horizontal wall 40c is an arced wall that is curved outwardly. When operating the handle 14, the user places a thenar muscle region 2 on the horizontal wall 40c and the vertical wall 40a that is located at the side opposite to the handle 14. Further, the vertical wall 40b located closer to the handle 14 serves as a restriction that restricts excess pivoting of the handle 14 by coming into contact with the pivoted handle 14.

In the main body 11, a recess 41 is formed between the bottle attaching portion 21 and the support 40. Specifically, the recess 41 is sloped such that the horizontal wall 40c gradually approaches the bottle attaching portion 21. The base of the index finger of the user is placed in the recess 41.

The operation of the breast pump 1 will now be described.

As shown in FIG. 1 and FIG. 3, the breast pump 1 is directed so that the hood 13 faces the breast of a user to pump milk. The user places fingers other than the thumb on the handle 14 from below. When operating the handle 14, the user places the thenar muscle region 2 on the vertical wall 40a, which is located at the side opposite the handle 14, and the horizontal wall 40c of the support 40. Also, the user places the base of the index finger in the recess 41 and the thumb on the upper side of the hood attaching portion 22. In this manner, the breast pump 1 is held by the user in a supination position. When the hood 13 is fitted to the breast of the user so as to close the milking port 13c, the internal passage 23 becomes a substantially sealed space. In this case, the handle base 15 is guided by the guide portion 33 and the handle 14 is rotated about the connection projection 32 relative to the main body 11 in conformance with the body of the user or the like. This allows for easy handle operation by the user.

Figure 4:
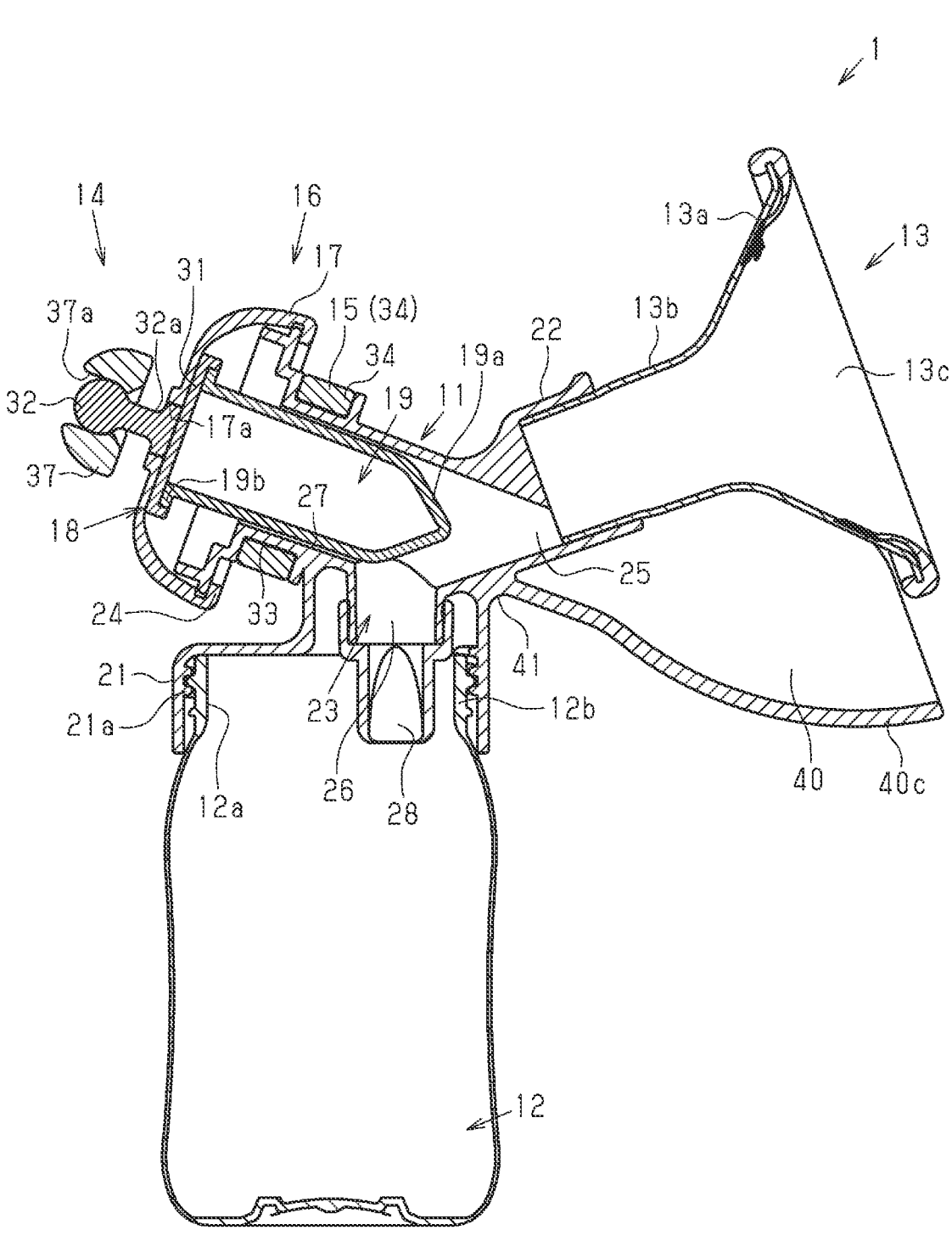
FIG. 4 is a cross-sectional view of the breast pump shown in FIG. 1 when the internal passage is in a negative pressure state.
Figure 5:
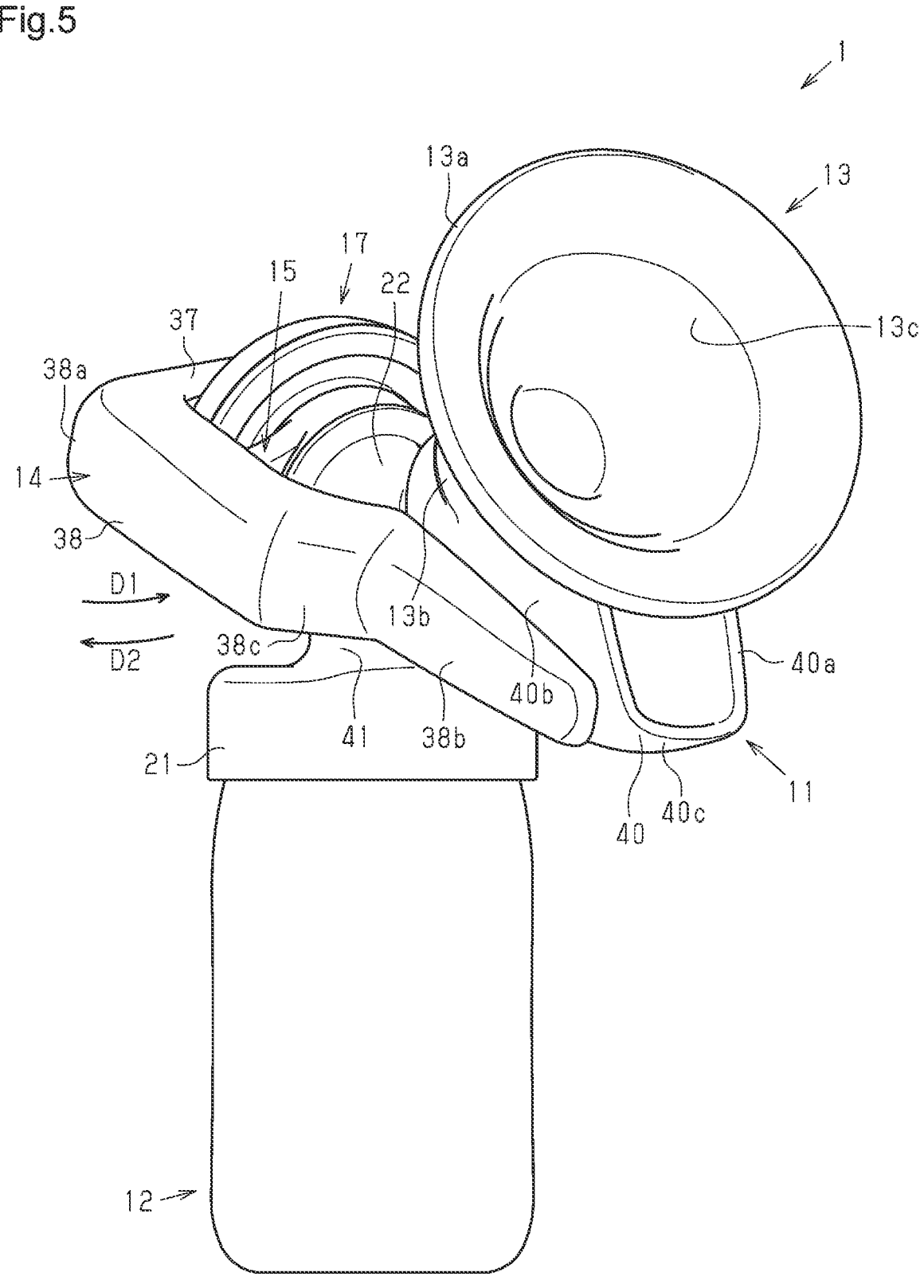
FIG. 5 is a perspective view of the breast pump shown in FIG. 1 when a handle is pivoted.

As shown in FIG. 4, when the handle 14 is pivoted in arrowed direction D1, the diaphragm 17 is lifted by the lift plate 18. This forms a negative pressure state in the internal passage 23, and pumped milk flows from the inflow passage 25 into the temporary reservoir 26. In a negative pressure state, the bottom of the temporary reservoir 26 is closed by the valve member 28. Accordingly, the milk flowing from the inflow passage 25 collects in the temporary reservoir 26. As shown in FIG. 5, the handle 14 is pivoted until the handle 14 contacts the vertical wall 40b of the support 40.

When the user reduces the squeezing force, the resiliency of the diaphragm 17 pivots the handle 14 in arrowed direction D2 and returns the internal passage 23 to normal pressure. This opens the valve member 28 of the temporary reservoir 26, and milk flows into the bottle 12. The handle 14 is repetitively moved back and forth to pump milk. In this case, the insertion portion 19a is also reciprocated inside the negative pressure generation passage 27. The insertion portion 19a reduces the volume of the negative pressure generation passage 27. Thus, the pressure that changes when the diaphragm 17 is deformed is subtly affected.

The gap formed between the outer circumferential surface of the insertion portion 19a and the inner circumferential surface of the negative pressure generation passage 27 allows for smooth reciprocation of the insertion portion 19a. The user grips the handle 14 with four fingers other than the thumb from below to pivot and operate the handle 14. Accordingly, the handle 14 receives a force acting to lower the lever 38. The handle 14 is connected to the insertion member 19 by the lift plate 18, and the insertion member 19 is supported by the inner circumferential surface of the negative pressure generation passage 27 with a slight gap formed between the outer circumferential surface of the insertion portion 19a and the inner circumferential surface of the negative pressure generation passage 27. Thus, the insertion member 19 is stably supported by the inner circumferential surface of the negative pressure generation passage 27. As a result, the insertion member 19, which is supported by the negative pressure generation passage 27 further supports the pivot point and allows for stable pivoting of the handle 14. This reduces load applied to the portion connecting the engagement hole 37b and the connection projection 32, which connects the handle 14 and the lift plate 18.

The inventors of the present invention tested the advantages of the breast pump 1 as described below. The breast pump 1 according to the present invention and a conventional breast pump were used to measure the forearm position of the right arm and the muscle electric potential. As shown in FIGS. 6A and 6B, the conventional breast pump is a model for the pronation position, and the breast pump 1 is a model for the supination position. FIG. 7 shows the muscle electric potential in the extensor carpi radialis muscle when using the conventional breast pump in a pronation position and when using the breast pump 1 in a supination position. Muscle activity during use of the breast pump 1 was reduced in the extensor carpi radialis muscle that is located in the forearm for radial flexion of the wrist joint. FIG. 8 shows the muscle electric potential in the thenar muscle when using the conventional breast pump in a pronation position and when using the breast pump 1 in a supination position. Muscle activity during use of the breast pump I was reduced in the thenar muscle that is located in the palm for bending/flexing of the thumb and gripping of the palm.

The breast pump 1 has the advantages described below.

(1) The breast pump 1 allows the user to pump milk with the forearm in a supination position. This reduces the load applied to the muscles of the forearm.

(2) The handle 14 includes the finger bump 38c adjacent to the pivot point side of the finger rest 38b. Thus, the user can operate the handle 14 with four fingers excluding the thumb. Further, the finger bump 38c prevents the side (base) of the index finger from contacting the main body.

(3) The user can place the thenar muscle region 2 on the support 40. This reduces the load applied to the thenar muscle of the user.

(4) Contact of the handle 14 with the vertical wall 40b of the support 40 limits the pivoting range.

(5) The base of the index finger can be engaged with the recess 41. This stabilizes the position of the breast pump 1 when held in a supination position.

(6) The insertion portion 19a is supported by the negative pressure generation passage 27. This reduces the load applied to the pivot point of the handle 14 when the handle 14 is being repetitively pivoted.

(7) Even though the diameter of the negative pressure generation passage 27 is increased to allow the internal passage 23 to be cleaned easily, the insertion portion 19a is inserted into the negative pressure generation passage 27, which has a relatively large diameter. Thus, the volume of the internal passage 23 is not increased. This maintains the milk-pumping efficiency without affecting the changing of pressure in the internal passage 23.

(8) The insertion member 19 is fixed to and integrated with the lift plate 18 as a single component. This facilitates cleaning and assembling/disassembling.

The above-described embodiment may be modified as follows.

The negative pressure generation passage 27 may be tilted in the pivoting direction of the handle 14 with respect to a direction in which the center axis of the support 40 or the attachment end 24 of the hood 13 extends. When the handle 14 is pivoted in arrowed direction D1, the handle 14 lifts the diaphragm 17 using the lift plate 18 in a direction intersecting the direction perpendicular to the main surface of the diaphragm 17 instead of the direction perpendicular to the main surface of the diaphragm 17. The insertion member 19 is also reciprocated in a direction tilted in accordance with the lifting direction of the diaphragm 17. Thus, the tilting of the negative pressure generation passage 27, into which the insertion portion 19*a* is inserted, in the same manner will result in further facilitated pivoting of the handle 14. This also allows the gap to be reduced between the outer circumferential surface of the insertion portion 19*a* and the inner circumferential surface of the negative pressure generation passage 27. Therefore, the volume of the internal passage 23 will not be increased.

The lift plate 18 may be formed integrally with the insertion member 19 as a single component. This decreases the number of parts.

The lift plate 18 may be fixed to the outer surface of the diaphragm 17 through adhesion or the like. In this case, the insertion portion 19*a* is integrally arranged on the inner surface of the diaphragm 17.

The lift plate 18 may be omitted, and the connection projection 32 may be arranged on the outer surface of the diaphragm 17 as a portion engaged with the engagement hole 37*b* of the handle 14.

The insertion portion 19*a* may be separated from the diaphragm 17. In this case, in an example, the insertion portion 19*a* is connected to the attachment flange 19*b* by a spacer that maintains a constant distance between the insertion portion 19*a* and the attachment flange 19*b*. Alternatively, the insertion portion 19*a* is connected to the plate portion 31 of the lift plate 18 by a spacer. In an example, the spacer may be formed by one or more linear members or shafts that connect the insertion portion 19*a* and the attachment flange 19*b* or the plate portion 31.

The attachment flange 19*b* may be omitted, and the insertion portion 19*a* may be formed integrally with the diaphragm 17 as a single component. This structure also decreases the number of parts.

The distal end surface of the insertion portion 19*a* does not have to have a protruding triangular shape and may be, for example, flat or recessed.

The outer circumferential surface of the insertion portion 19*a* may have any form as long as the volume of the negative pressure generation passage 27 is reduced. For example, in side view, the circumferential surface of the insertion portion 19*a* may be corrugated, concave, or convex.

The projecting shape of the insertion portion 19*a* does not have to correspond to the internal shape of the negative pressure generation passage 27, into which the insertion portion 19*a* is inserted. For example, the projecting shape (outer shape) of the insertion portion 19*a* may be a polygonal post such as a triangular post, a square post, and a hexagonal post, and the negative pressure generation passage 27 may have the form of a hollow cylinder. Alternatively, the projecting shape of the insertion portion 19*a* may be a column or a cylinder, and the internal shape of the negative pressure generation passage 27 may correspond to a polygonal post such as a triangular post, a square post, and a hexagonal post.

The insertion member 19 may be omitted. When the insertion member 19 is omitted, the negative pressure generation passage 27 does not have to be increased in diameter in conformance with the insertion portion 19*a*. Instead, it is preferred that the internal passage 23 be decreased in diameter to avoid increases in the volume.

The structure of the internal passage 23 is not limited. For example, the temporary reservoir 26 may be omitted. In this case, the valve member 28 may be omitted.

The recess 41 may be omitted from the main body 11. In this case, other stable-support means may be arranged so that the breast pump 1 is held stably in a supination position.

The vertical wall 40*b* of the support 40 does not have to act as a restriction that limits the pivoting range of the handle 14. For example, a projection may be arranged near the pivot shaft 36 of the handle base 15 or the shaft support 39 of the handle 14 to limit the pivoting range of the handle 14.

The support 40 of the main body 11 does not have to be disposed directly below the hood 13. For example, the support 40 may be inclined toward or away from the handle 14. Further, the support 40 may be omitted.

Instead of forming a gap between the outer circumferential surface of the insertion portion 19*a* and the inner circumferential surface of the negative pressure generation passage 27, the insertion portion 19*a* may include a syringe-like rubber piston that is arranged at the distal end of the insertion portion 19*a* and tightly fitted to the negative pressure generation passage 27 in order to generate negative pressure in the internal passage 23.

The handle 14 may be directly supported by the main body 11 in a pivotal manner instead of being supported by the handle base 15. In this case, the pivot support piece 35, the pivot shaft 36, and the like are integrated with the main body 11.

Figure 9:
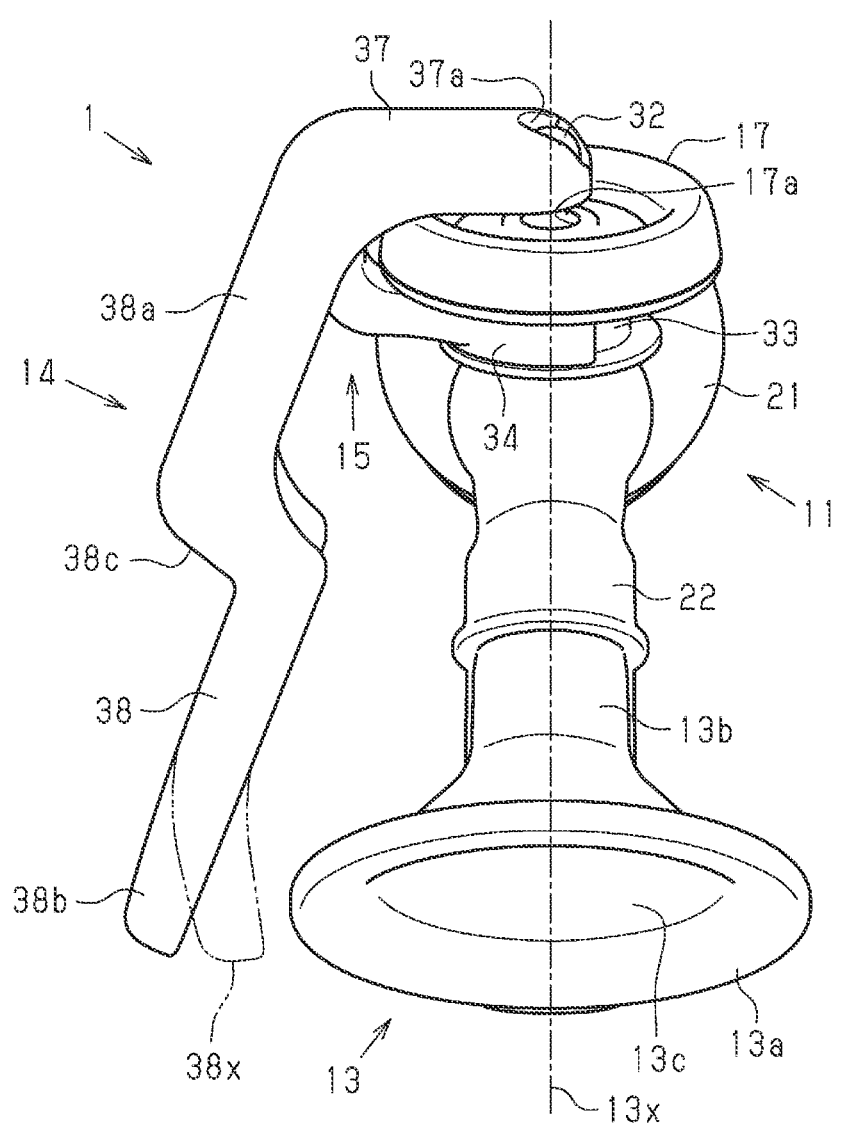
FIG. 9 is a plan view of the breast pump shown in FIG. 1.

In the above example, the finger rest 38*b* of the handle 14 is entirely linear. Alternatively, as shown in FIG. 9, the finger rest 38*b* may include a distal end 38*x* (dotted line) that is curved toward the center line 13*x* of the hood 13. This allows the little finger, which is placed on the distal end of the finger rest 38*b*, to be located close to the thenar eminence for handle operation. The finger rest 38*b* may be entirely curved toward the center line 13*x* of the hood 13.

In the above example, the breast pump 1 is described as for use by a right-handed user. In case for a left-handed user, the handle 14 only needs to extend at the opposite side of the main body 11 in FIG. 1.

The handle 14 and the hood 13 may fully extend in the same direction. Further, the handle 14 may extend diagonally upward instead of diagonally downward with respect to the main body 11.

The bottle 12 does not have to be attachable to and detachable from the bottle attaching portion 21 and may be formed integrally with the bottle attaching portion 21. Further, the hood 13 does not have to be attachable to and detachable from the hood attaching portion 22 and may be formed integrally with the hood attaching portion 22.

The inflow passage 25 and the temporary reservoir 26 may also have a diameter allowing a user can insert, for example, a finger.

REFERENCE SIGNS LIST 1) breast pump, 2) thenar muscle region, 11) main body, 12) bottle, 12a) open bottle portion, 12b) external thread, 13) hood, 13a) large-diameter portion 13b) cylindrical portion, 13c) milking port, 13x) center line, 14) handle, 15) handle base, 16) negative pressure generation mechanism, 17) diaphragm, 17a) through hole, 18) lift plate, 19) insertion member, 19a) insertion portion, 19b) attachment flange, 21) bottle attaching portion, 21a) internal thread, 22) hood attaching portion, 23) internal passage, 24) attachment end, 25) inflow passage, 26) temporary reservoir, 27) negative pressure generation passage, 28) valve member, 31) plate portion, 32) connection projection, 32a) engagement groove, 33) guide portion, 34) attachment portion, 35) pivot support piece, 36) pivot shaft, 37) lifter, 37a) pit, 37b) engagement hole, 38) lever, 38a) curved part, 38b) finger rest, 38c) finger bump, 38x) distal end, 39) shaft support, 40) support, 40a) vertical wall, 40b) vertical wall, 40c) horizontal wall, 41) recess.

The invention claimed is:

1. A breast pump, comprising:
a main body including:
  an internal passage;
  a diaphragm configured to generate negative pressure in the internal passage for pumping milk, wherein the diaphragm closes an end of the internal passage;
  a lift plate arranged on the diaphragm and connected to a handle; and an insertion member attached to the lift plate and inserted into the internal passage, wherein the insertion member comprises an insertion portion having a projecting shape corresponding to an internal shape of the internal passage;
a hood attaching portion to which a hood configured to be fitted to a breast is attached, the hood attaching portion being disposed at a front part of the main body; and
a bottle attaching portion to which a bottle for collecting milk is attached, the bottle attaching portion being disposed at a lower part of the main body, wherein the handle is pivotal to the main body and includes a basal end connected to the lift plate, and wherein the handle includes a finger rest at a distal end of the handle and extends from a pivot point of the handle in a forward direction relative to the main body.

2. The breast pump according to claim 1, wherein the handle includes a finger bump arranged at a side of the finger rest adjacent to the pivot point.

3. The breast pump according to claim 1, wherein the finger rest is entirely linear or includes at least a part curved toward the hood.

4. The breast pump according to claim 1, wherein the main body includes a support disposed below the hood.

5. The breast pump according to claim 4, wherein the support is a restriction configured to limit a pivoting range of the handle.

6. The breast pump according to claim 4, wherein the main body includes a recess formed between the bottle attaching portion and the support.

\* \* \* \* \*